United States Patent
Swartout et al.

(10) Patent No.: US 7,112,909 B2
(45) Date of Patent: Sep. 26, 2006

(54) METHOD AND SYSTEM FOR MEASURING WEDGE TIGHTNESS

(75) Inventors: Richard Neil Swartout, Crossville, TN (US); Leonard George Pezzano, Atlanta, GA (US)

(73) Assignee: General Electric Company, Schenectady, NY (US)

( * ) Notice: Subject to any disclaimer, the term of this patent is extended or adjusted under 35 U.S.C. 154(b) by 326 days.

(21) Appl. No.: 10/780,178

(22) Filed: Feb. 17, 2004

(65) Prior Publication Data

US 2005/0284241 A1    Dec. 29, 2005

(51) Int. Cl.
    H02K 15/02    (2006.01)
(52) U.S. Cl. ................................. 310/214
(58) Field of Classification Search .......... 310/214
    See application file for complete search history.

(56) References Cited

U.S. PATENT DOCUMENTS

| | | | |
|---|---|---|---|
| 4,055,826 A | 10/1977 | Franz | |
| 4,422,320 A * | 12/1983 | Moorby et al. | 73/12.09 |
| 4,675,670 A * | 6/1987 | Lalonde et al. | 340/870.37 |
| 4,853,565 A * | 8/1989 | Elton et al. | 310/45 |
| 4,889,000 A * | 12/1989 | Jaafar et al. | 73/865.8 |
| 5,012,684 A * | 5/1991 | Humphries | 73/865.8 |
| 5,020,234 A * | 6/1991 | Alkire et al. | 33/656 |
| 5,295,388 A * | 3/1994 | Fischer et al. | 73/12.09 |
| 6,268,668 B1 | 7/2001 | Jarczynski et al. | |
| 6,421,914 B1 | 7/2002 | Iversen et al. | |
| 6,584,680 B1 | 7/2003 | Iversen et al. | |
| 6,631,335 B1 | 10/2003 | Lusted et al. | |
| 2004/0135588 A1* | 7/2004 | Bissonnette et al. | 324/662 |

FOREIGN PATENT DOCUMENTS

| EP | 415042 A2 * | 3/1991 |
|---|---|---|
| EP | 553968 A2 * | 8/1993 |

* cited by examiner

*Primary Examiner*—Burton Mullins
(74) *Attorney, Agent, or Firm*—Armstrong Teasdale LLP

(57) ABSTRACT

A method for measuring wedge tightness in an electromechanical device includes providing a top ripple spring that includes a conductive portion and a non-conductive portion, positioning the top ripple spring at least partially within a stator slot defined within the electromechanical device, mapping a profile of the top ripple spring, and using the mapped profile to determine the wedge tightness in the electromechanical device.

17 Claims, 5 Drawing Sheets

METHOD AND SYSTEM FOR MEASURING WEDGE TIGHTNESS

BACKGROUND OF THE INVENTION

This invention relates generally to electrical power generators and more particularly, to methods and system for detecting wedge tightness in an electrical power generator.

Armature windings, also known as stator bar windings, are routinely inspected in at least some known electrical power generators, to verify their operation. In some known generators, a stator yoke in the generator surrounds an armature core and partially encloses the armature windings. The stator windings are formed from a plurality of copper conductors that are wound in the armature to form loops. The armature windings may be arranged within a stator slot in such a manner that desired voltage and current characteristics may be maintained by the generator during operation.

At least one known generator includes a wedge system to induce a radial retaining force (RRF) to the stator from wedges to facilitate reducing movement of the stator bar windings within the stator slot. However, if the wedge system itself becomes loose, the amount of RRF is reduced such that the stator bar windings may move during operation. Over time, the relative motion of the stator bar windings cause damage to insulation surrounding the stator bar wedges, an/or a potential stator bar winding failure through electrical shorts to ground. Accordingly, within known generators, the wedge system is periodically inspected to determine if any stator bar winding movement within the stator slots exceeds predetermined tolerances.

Currently, several known methods of assessing the status of a wedge system are used. A first known method uses a hardness tester to assess the relative looseness of the stator wedges. A second known method requires tapping each individual wedge and listening to the response to determine whether the wedges are loose. A third known method includes exciting the vibrational modes of the stator wedges using multiple impacts, and receiving the energy transmitted from the multiple impacts using a band-pass filter to determine whether the wedges are loose. However, when the wedge system includes a top ripple spring, the above-described wedge system inspection methods may not accurately determine the tightness of the wedge system within the stator slot over the full range of operational wedge pressures when a top ripple spring system is used.

BRIEF DESCRIPTION OF THE INVENTION

In one aspect, a method for measuring wedge tightness in an electromechanical device is provided. The method includes providing a top ripple spring that includes a conductive portion and a non-conductive portion, positioning the top ripple spring at least partially within a stator slot defined within the electromechanical device, mapping a profile of the top ripple spring, and using the mapped profile to determine the wedge tightness in the electromechanical device.

In another aspect, a stator wedge measurement system is provided. The system includes a top ripple spring including a conductive portion and a non-conductive portion, wherein the top ripple spring is positioned at least partially within a stator slot, and a measuring apparatus for mapping a profile of the top ripple spring, the measuring apparatus is configured to determine the wedge tightness in an electromechanical device based on the mapped profile.

In a further aspect, an electric generator is provided. The generator includes a plurality of top ripple springs including a conductive portion and a non-conductive portion, each said top ripple spring positioned at least partially within each respective stator slot, and a measuring apparatus for mapping a profile of each top ripple spring, the measuring apparatus configured to determine the wedge tightness in the electric generator based on the mapped profile.

DETAILED DESCRIPTION OF THE INVENTION

Figure 1:
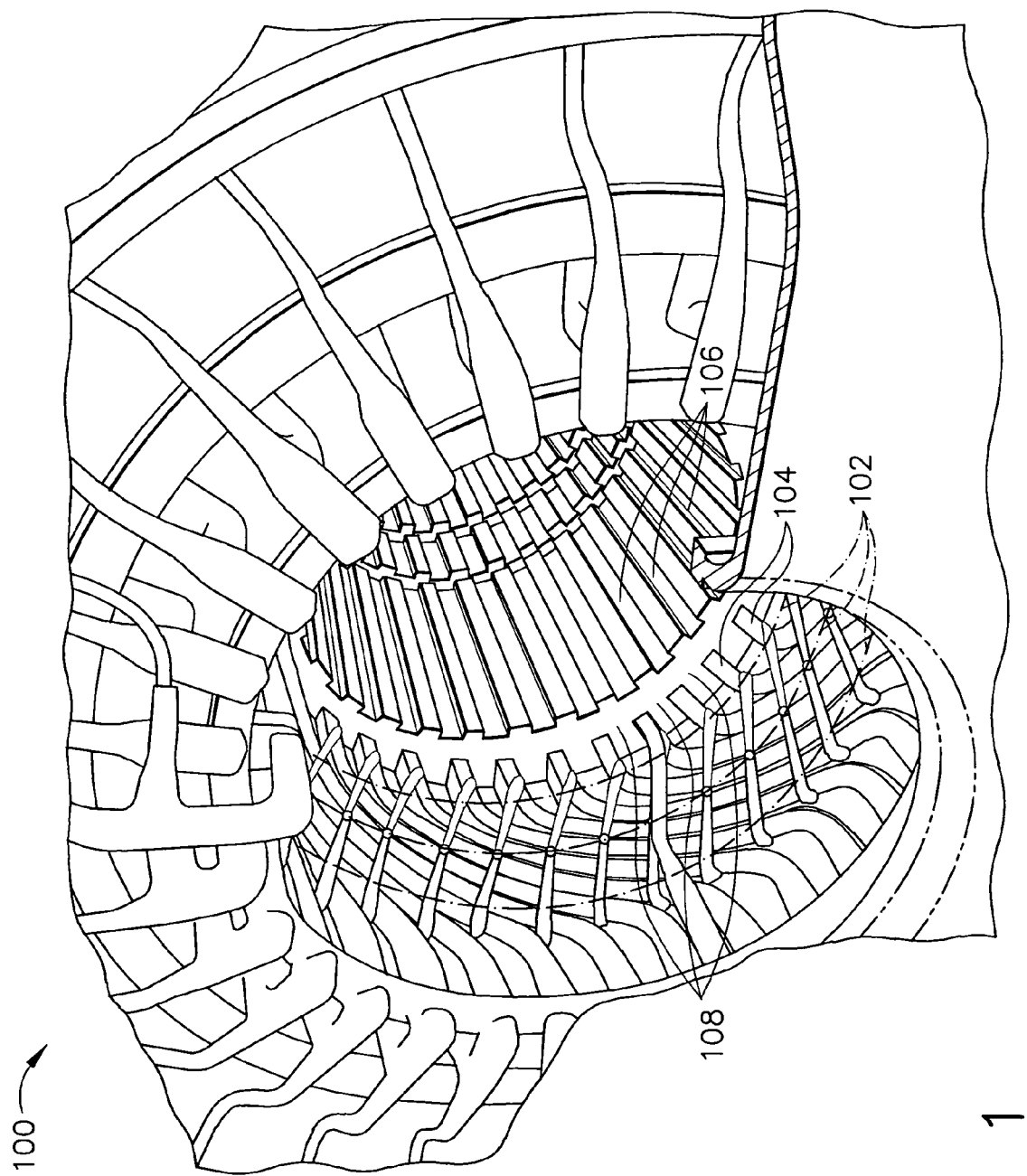
FIG. 1 is a perspective end view of an exemplary electric generator.

FIG. 1 is a perspective end view of an exemplary electric generator 100. A rotor 102 is transparently represented by dashed lines. A plurality of stator bar windings 104 are positioned in slots 106 defined around an inner circumference of a stator core 108. In the exemplary embodiment, stator bars windings 104 are formed from a plurality of flat bar conductors or stator bars that are coupled together to form a pre-determined winding path through winding 104. In one embodiment, the stator bars are fabricated from copper.

Figure 2:
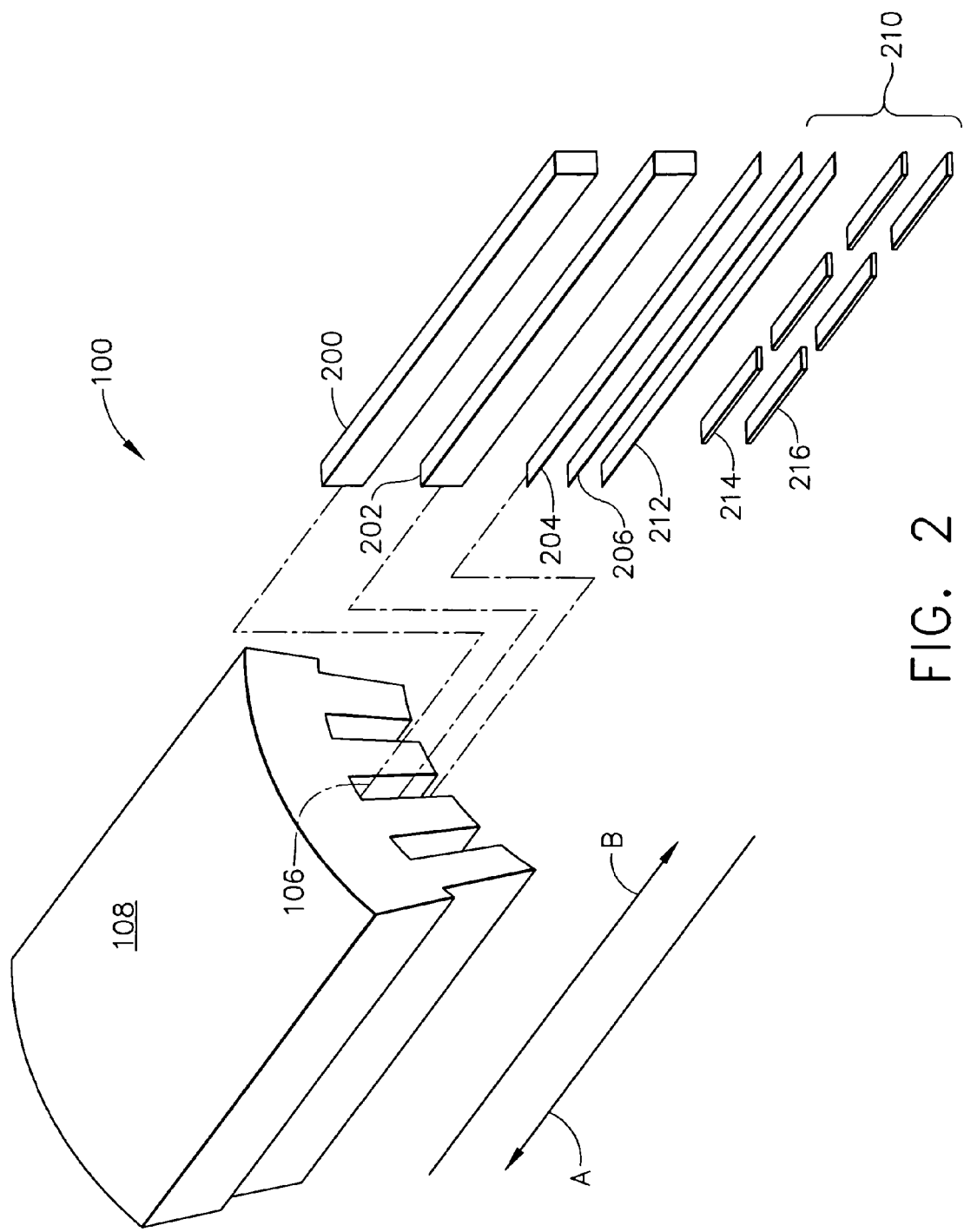
FIG. 2 is a partial exploded view of a portion of electric generator stator shown in FIG. 1.

FIG. 2 illustrates a partial exploded view of a portion of electric generator 100. In the exemplary embodiment, an outer stator bar winding 200, an inner stator bar winding 202, and one or more slot fillers 204, 206 are positioned at least partially within each slot 106. A wedge system 210, including a top ripple spring 212, is then positioned at least partially within stator slot 106 such that top ripple spring 212 is adjacent at to at least one of slot filler 204 or slot filler 206. Top ripple spring 212 is then secured in stator slot 106 using a plurality of stator wedge slides 214 and stator wedges 216.

For example, moving stator wedge slides 214 in a first direction, indicated by arrow A, and with respect to stator wedges 216, or moving stator wedges 216 in a second direction, indicated by arrow B, with respect to stator wedge slides 214, induces restraining pressure to outer stator bar 200 and inner stator bar 202 to facilitate securing outer stator bar 200 and inner stator bar 202 within stator slot 106.

Figure 3:
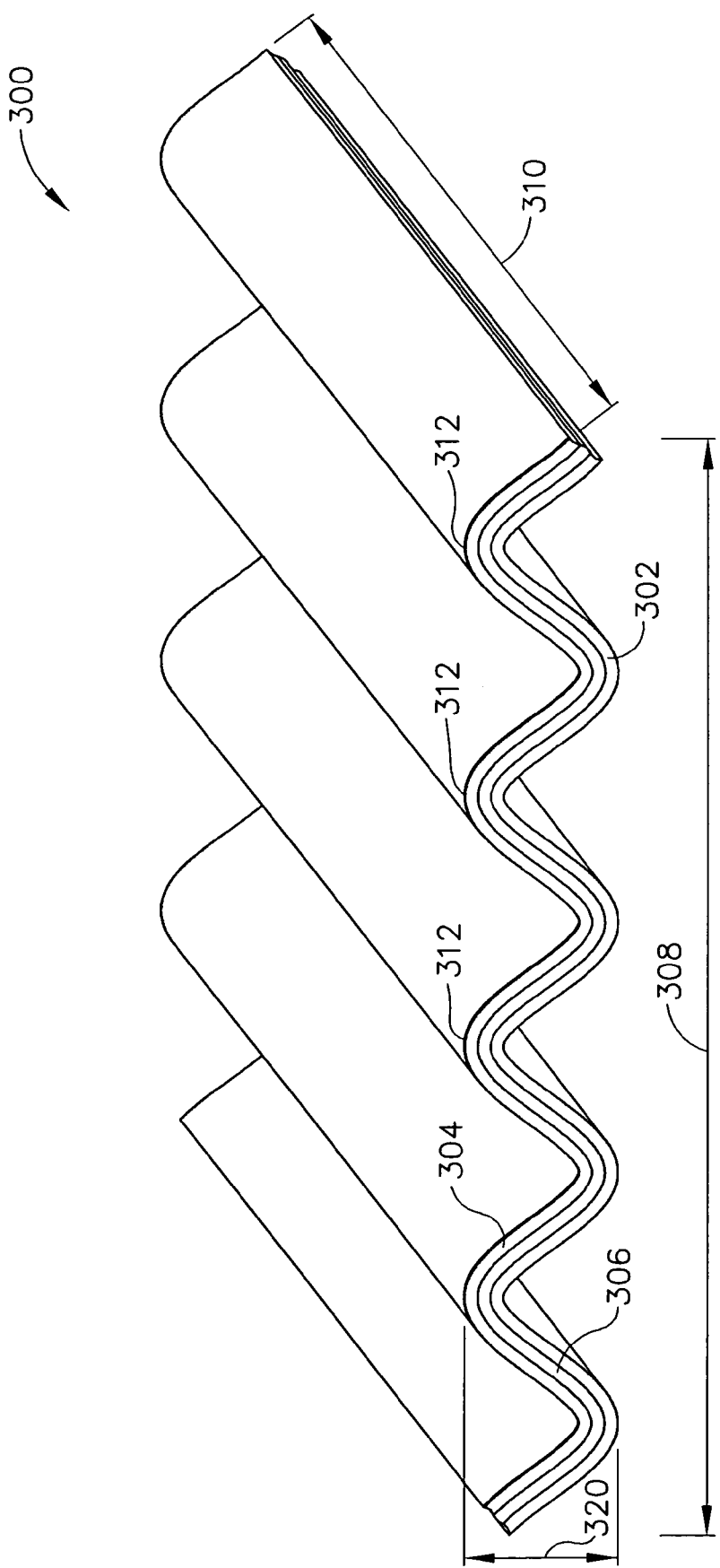
FIG. 3 is a side view of an exemplary top ripple spring that may be used with the electric generator shown in FIG. 1.

FIG. 3 is a side view of top ripple spring 212. In the exemplary embodiment, top ripple spring 212 includes a bottom portion 302 and an oppositely disposed top portion 304 that extends substantially parallel to bottom portion 302. Top ripple spring 212 also includes a conductive element 306 positioned between top portion 304 and bottom portion 302. In the exemplary embodiment, top portion 304 and bottom portion 302 are fabricated from a non-conductive material such as, but not limited to, a plastic laminate. Conductive element 306 is fabricated from a metallic material such as, but not limited to, a metallic foil. Conductive element 306 has a cross-sectional profile that is substantially similar to the cross-sectional profile of bottom portion 302 and top portion 304 such that conductive element 306 substantially mates against top and bottom portion 304 and 302, respectively. Moreover, top ripple spring 212 has a length 308 and a width 310 that are variably selected depending on the size of stator slot 106 (shown in FIG. 2). Top ripple spring 212 also includes a plurality of projections 312 that are arranged in a cyclic pattern and extend lengthwise and widthwise across top ripple spring 212 in a longitudinal-axial configuration. In an alternative embodiment, projections 312 are arranged in a different pattern relative to top ripple spring 212. In the exemplary embodiment, each projection 312 has a substantially semi-circular cross-sectional profile. Alternatively, each projection 312 has a non-semi-circular cross-sectional profile. For example, in an alternative embodiment, projections 312 have at least one of a circular, and a triangular cross-sectional profile.

During use, top ripple spring 212, including conductive element 306, is positioned at least partially within stator slot 106, and stator wedges 216 are then inserted into stator slot 106 to induce a compression force on top ripple spring 212. More specifically, stator wedges 216 are repositioned to facilitate compressing top ripple spring 212 substantially flat, at which time a full radial retaining force is achieved. For example, in the exemplary embodiment, when top ripple spring 212 is not compressed, i.e., top ripple spring 212 is relaxed, a thickness 320 of top ripple spring 212 is between approximately sixty mils (one-thousandth of an inch) and approximately sixty-five mils. More specifically, top ripple spring 212 has an approximately thirty mil deflection when top ripple spring 212 is not compressed. However, when top ripple spring 212 is compressed by wedges 216, top ripple spring 212 is compressed to a thickness 320 between approximately four mils and approximately six mils.

Accordingly, as the pressure on top ripple spring 212 is increased (or decreased) by repositioning wedges 216 within stator slot 106, thickness 320 of top ripple spring 212 changes across stator slot 106 in response to the wedge pressure increase (or decrease). Accordingly, since top ripple spring thickness 320, when either compressed or uncompressed is both predictable and measurable, a measuring instrument can be used to map a profile of top ripple spring 212. The measured profile is then used to determine the tightness of wedges 216 within stator slot 106.

Figure 4:
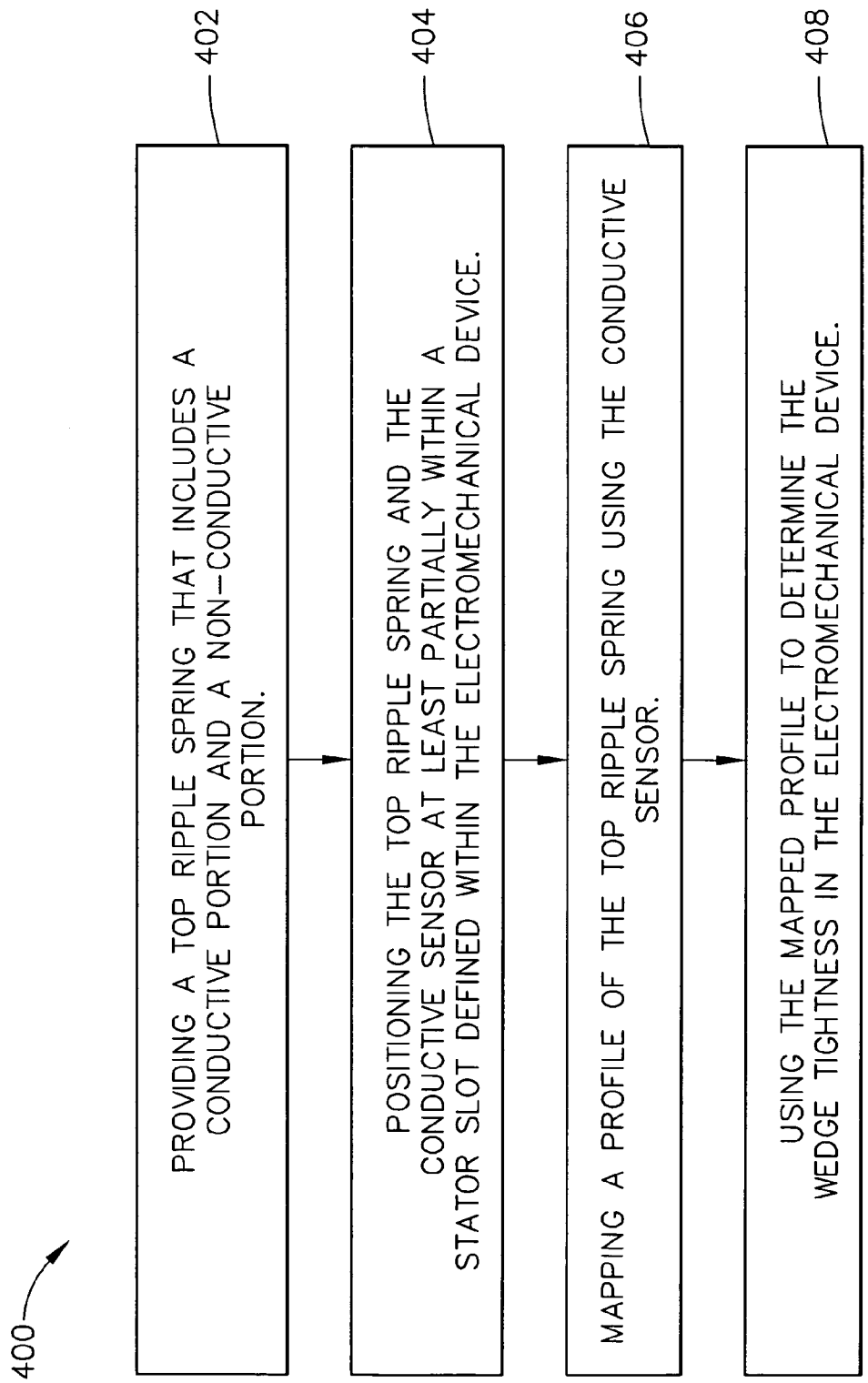
FIG. 4 is an exemplary method for measuring wedge tightness in an electromechanical device such as the electric generator shown in FIG. 1.

FIG. 4 is an exemplary method 400 for measuring wedge tightness in an electromechanical device such as, but not limited to, electric generator 100 (shown in FIG. 1). Method 400 includes fabricating 402 a top ripple spring, the top ripple spring including a conductive portion and a non-conductive portion, positioning 404 the top ripple spring and the conductive sensor at least partially within a stator slot; mapping 406 a profile of the top ripple spring using the conductive sensor, and using 408 the mapped profile to determine the wedge tightness in the electromechanical device.

Figure 5:
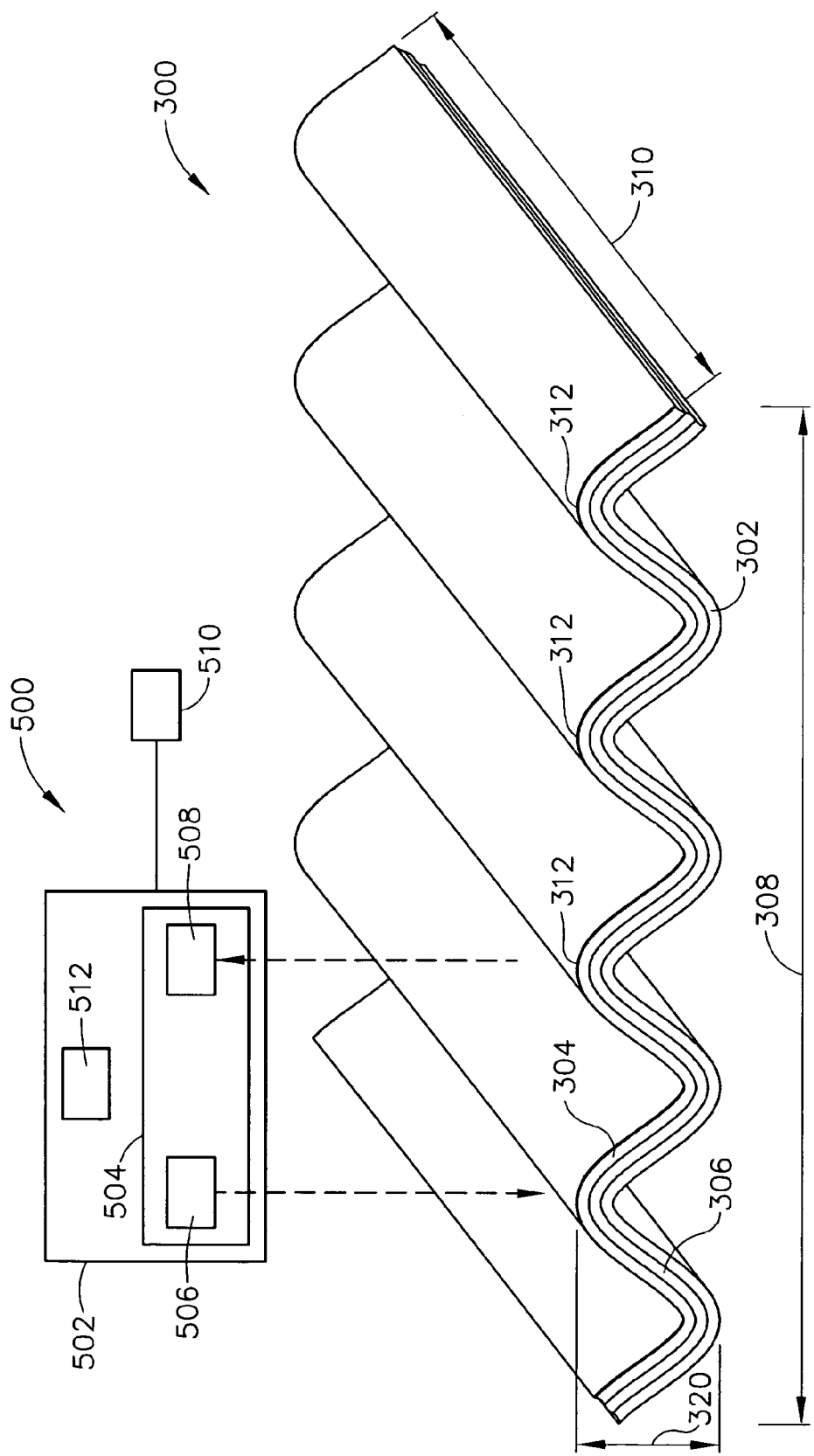
FIG. 5 is an exemplary measuring system that may be used to measure wedge tightness in an electromechanical device.

FIG. 5 is an exemplary measuring system 500 that can be used to measure the wedge tightness in an electromechanical device such as, but not limited to, electric generator 100 (shown in FIG. 1). Measuring system 500 includes a measuring apparatus 502. In the exemplary embodiment measuring apparatus 502 is a transceiver and includes an inductive sensor 504 including an excitation coil 506 and a sensing coil 508. In one embodiment, measuring system 500 also includes a computer 510 configured to receive information from measuring apparatus 502. In another embodiment, measuring apparatus 502 includes a computer 512 configured to analyze data received from sensing coil 508.

As used herein, the term computer is not limited to just those integrated circuits referred to in the art as computers, but broadly refers to computers, processors, microcontrollers, microcomputers, programmable logic controllers, application specific integrated circuits, and other programmable circuits.

In operation, measuring system 500 is energized such that an energy is transmitted from excitation coil 506. Measuring apparatus 502 is than transitioned in an axial direction along each stator slot 106. As measuring apparatus 502 is transitioned along stator slot 106, sensing coil 508 receives energy reflected from conductive element 306. In the exemplary embodiment, the voltage received at sensing coil 508 is approximately proportional to the proximity of conductive element 306 to sensing coil 508. More specifically, as measuring apparatus 502 transitions along stator slot 106, measuring apparatus 502 receives a voltage from conductive element 306 that is approximately proportional to the top ripple spring profile. The top ripple spring profile is then mapped using measuring apparatus 502, or computer 510 coupled to measuring apparatus 502 for example, to determine a thickness or relaxation of top ripple spring 212. The thickness or relaxation measurement of top ripple spring 212 is then used to determine the wedge tightness in the electromechanical device.

When applied to a full range of wedge pressures, the methods described herein facilitate allowing an operator to easily inspect an electromechanical device wedge system to determine the tightness of the wedge system in the stator slot. Specifically, the methods described herein facilitate measuring the tightness of the wedges accurately over the full range of operational wedge pressures when a top ripple spring system is used. The mapped profile can then be used by an operator to determine if the wedges need tightening, or estimate when the wedges will require tightening in the future.

Exemplary embodiments of wedge systems used in an electromechanical device are described above in detail. The components are not limited to the specific embodiments described herein, but rather, components of the wedge system may be utilized independently and separately from other components described herein. Specifically, the top ripple spring and conductive element described herein can also be used in combination with other wedge systems components installed in a plurality of electromechanical devices.

While the invention has been described in terms of various specific embodiments, those skilled in the art will recognize that the invention can be practiced with modification within the spirit and scope of the claims.

What is claimed is:

1. A method for measuring wedge tightness in an electromechanical device, said method comprising:
    providing a top ripple spring that includes a conductive portion and a non-conductive portion;
    positioning the top ripple spring at least partially within a stator slot defined within the electromechanical device;
    mapping a profile of the top ripple spring via transmitting energy from an excitation coil to the conductive portion of the top ripple spring, and receiving, energy reflected from the conductive portion using a sensing, coil; and
    using the mapped profile to determine the wedge tightness in the electromechanical device.

2. A method in accordance with claim 1 wherein the mapped profile corresponds to a particular pressure on the top ripple spring.

3. A method in accordance with claim 1 wherein measuring wedge tightness in an electromechanical device comprises measuring wedge tightness in an electrical generator.

4. A method in accordance with claim 1 further compressed inserting at least one wedge into the stator slot until the top ripple spring is compressed between approximately four one-thousandths of an inch and six one-thousandths of an inch thick.

5. A method in accordance with claim 1 further comprising repositioning a measuring apparatus along the stator slot until the entire top ripple spring profile is mapped.

6. A method in accordance with claim 1 wherein providing a top ripple spring that includes a conductive portion further comprises providing a top ripple spring wherein the conductive portion has a profile that is substantially similar to a profile of the top ripple spring.

7. A stator wedge measurement system comprising:
a top ripple spring comprising a conductive portion and a non-conductive portion, said top ripple spring positioned at least partially within a stator slot;
a measuring apparatus for mapping a profile of the top ripple spring, said measuring apparatus configured to transmit energy from an excitation coil to said top ripple spring conductive portion, and receive energy reflected from said conductive portion using a sensing coil; and
said measuring apparatus further configured to determine the wedge tightness in an electromechanical device based on the mapped profile.

8. A stator wedge measurement system in accordance with claim 7 wherein said each said profile mapped of said top ripple spring by said measuring apparatus corresponds to a particular pressure induced on said top ripple spring.

9. A stator wedge measurement system in accordance with claim 7 wherein said measuring device is further configured to determine a wedge tightness in an electric generator.

10. A stator wedge measurement system in accordance with claim 7 further comprising at least one wedge configured to compress said top ripple spring until said top ripple spring is between approximately four one-thousandths of an inch and approximately six one-thousandths of an inch thick.

11. A stator wedge measurement system in accordance with claim 7 wherein said measurement apparatus is further configured to move along the stator slot during mapping of said top ripple spring.

12. A stator wedge measurement system in accordance with claim 7 wherein a profile of said top ripple spring conductive portion is substantially similar to a profile of said top ripple spring.

13. An electric generator comprising;
a stator comprising a plurality of slots;
a plurality of top ripple springs, each said top ripple spring comprising a conductive portion and a non-conductive portion, each said top ripple spring positioned at least partially within each said respective stator slot;
a measuring apparatus for mapping a profile of each said top ripple spring, said measuring apparatus configured to transmit energy from an excitation coil to said too ripple spring conductive portion, and receive energy reflected from said conductive portion using a sensing coil; and
said measuring apparatus for mapping a profile of each said top ripple spring, further configured to determine the wedge tightness in said electric generator based on the mapped profile.

14. An electric generator in accordance with claim 13 wherein each said profile mapped of said top ripple spring by said measuring apparatus corresponds to a particular pressure induced on said top ripple spring.

15. An electric generator in accordance with claim 13 further comprising at least one wedge configured to compress said top ripple spring until said top ripple spring is between approximately four one-thousandths of an inch and approximately six one-thousandths of an inch thick.

16. An electric generator in accordance with claim 13 wherein said measurement apparatus is further configured to move along said stator slot during mapping of said top ripple spring.

17. An electric generator in accordance with claim 13 wherein a profile of said top ripple spring conductive portion is substantially similar to a profile of said top ripple spring.

* * * * *

UNITED STATES PATENT AND TRADEMARK OFFICE
CERTIFICATE OF CORRECTION

PATENT NO. : 7,112,909 B2
APPLICATION NO. : 10/780178
DATED : September 26, 2006
INVENTOR(S) : Swartout et al.

It is certified that error appears in the above-identified patent and that said Letters Patent is hereby corrected as shown below:

In Claim 1, column 4, line 61, delete "receiving, energy" and insert therefor -- receiving energy --.
In Claim 1, column 4, line 62, delete "sensing, coil" and insert therefor -- sensing coil --.
In Claim 4, column 5, beginning on line 4, delete "compressed" and insert therefor -- comprising --.
In Claim 13, column 6, line 9, delete "comprising;" and insert therefor -- comprising: --.
In Claim 13, column 6, line 17, delete "to said too" and insert therefor -- to said top --.
In Claim 13, column 6, line 22, delete "spring, further" and insert therefor -- spring further --.

Signed and Sealed this

Twenty-seventh Day of May, 2008

JON W. DUDAS
*Director of the United States Patent and Trademark Office*